United States Patent [19]  [11] 4,450,175
Warshaw  [45] May 22, 1984

[54] METHOD AND COMPOSITIONS FOR TREATING ACNE

[76] Inventor: Thelma G. Warshaw, 519 E. Broad St., Westfield, N.J. 07960

[21] Appl. No.: 422,293

[22] Filed: Sep. 23, 1982

[51] Int. Cl.³ .............................................. A61K 31/04
[52] U.S. Cl. .................................................... 424/349
[58] Field of Search .......................................... 424/349

[56] References Cited

U.S. PATENT DOCUMENTS 4,254,145 3/1981 Birnbaum ............................ 424/305
4,291,015 9/1981 Keith et al. ........................... 426/28
4,322,433 3/1982 Leslie et al. .......................... 424/298

FOREIGN PATENT DOCUMENTS 964444 11/1964 United Kingdom .

OTHER PUBLICATIONS

Merck Index, 9th ed., 1976, p. 858, para. 6429.
The Physicians' Desk Reference, p. 768, "Nitrol", 26th ed., 1972.

Primary Examiner—Leonard Schenkman
Attorney, Agent, or Firm—Bruce M. Collins

[57] ABSTRACT

Acne is treated by the topical application of a vasodilating agent to loci of acne papules.

5 Claims, No Drawings

METHOD AND COMPOSITIONS FOR TREATING ACNE

DETAILED DESCRIPTION

The present invention pertains to a method of treating acne and to compositions useful in the practice of that method.

While presently not curable, acne can be successfully treated in many cases. Therapies currently in use or suggested, include the application of compositions containing such agents as benzoyl peroxide, sulfur, retinoic acid (including derivatives thereof) and salicylic acid. Many of these produce redness, peeling and desquamation of the treated skin and in addition, there is some evidence that benzoyl peroxide may have antibacterial action against *Propionibacterium acnes* (*P.acnes*), one of the two principal microorganisms associated with the condition.

The present invention is based on the discovery that the application of a topical vasodilator to the locus of a conglobate or dystic acne papule can effect a rapid improvement in the lesion. Vasodilators generally include smooth muscle relaxants such as nitrate esters of polyols (or derivatives of polyols) nitrites and the like. Such agents are often used in the treatment of the pain of angina pectoris and other spasms and include such compounds as amyl nitrite, glyceryl trinitrate, erythrityl tetranitrate, isosorbide dinitrate, mannitol hexanitrate, pentaerythritol tetranitrate, propatylnitrate, triethanolamine trinitrate, clonitrate and the like. Generally such agents have been administered for this purpose by the oral, sublingual or inhalation routes although systemic action upon transdermal administration utilizing polymeric diffusion matrices or biphasic lipophilic/hydrophilic carriers has been reported; see e.g., U.S. Pat. Nos. 4,291,015 and 4,322,433. The present method in contrast envisions and requires only local application and action at the loci of acne papules.

Without wishing to be bound by any theory of action, it appears the effectiveness of vasodilating nitrates and nitrites involves assisting the body's own defense against infection. *P. acnes* is a facultative anaerobic bacterium commonly found in acne papules and the presence of an anaerobic infection in otherwise healthy patients may be traceable to a temporary inadequacy in vascular supply in the rapidly enlarging pilosebaceous organ in which the acne process occurs. This impairment of vascular circulation not only may produce inadequate oxidation, permitting facultative anaerobes to thrive, but also reduce the effectiveness of *P. acnes* antibodies, titers of which generally parallel the clinical severity of the acne.

Whatever the mechanism of action, the effectiveness of the treatment can be readily observed in the clinic. In one study, twenty-five subjects suffering from severe acne presenting large (over 5 mm diameter) and tender papules applied to the loci of papules compositions containing 0.5 to 1% nitroglycerin in a homogeneous carrier comprising as its major components lanolin and petrolatum in a weight ratio of about 1:3. Application was made once a day, every morning. Such lesion when untreated generally persist in size and soreness for about three weeks. When so treated, the lesions decreased in size and tenderness in most cases after about 3 to 4 days.

TABLE

| Patient | Age/Sex | Diagnosis | Result |
|---|---|---|---|
| A | 23/M | cystic acne | cystic lesion cleared in 4 days |
| B | 18/M | acne fulminans | cleared large papule |
| C | 26/F | acne vulgaris | cleared treated cystic lesion |
| D | 52/F | acneform eruption | cleared large chin papules |
| E | 22/M | cystic acne | chest cystic lesion decreased |
| F | 18/M | acne vulgaris | leveled neck cyst |
| G | 20/M | conglobate acne | cyst growth reduced 50% |
| H | 26/F | acne vulgaris | leveled sore blemishes |
| I | 25/M | cystic acne | large lesions cleared in 7 days |
| J | 16/F | conglobate acne | new lesions cleared in 2 days |
| K | 20/F | cystic acne | no result-treatment abandoned |
| L | 19/F | acne vulgaris | 80% of cysts cleared over 3 weeks |
| M | 18/F | acne vulgaris | sore blemishes smaller in 1 day |
| N | 23/F | conglobate acne | slight size reduction in 7 days |
| O | 23/F | acne & seborrhea | no benefit |
| P | 31/F | acne & seborrhea | cleared five lesions |
| Q | 28/F | acne rosacea | treated cyst cleared |
| R | 30/F | acneform eruption | cyctic lesion cleared 4 days |
| S | 17/M | cystic acne | leveled cysts regularly |
| T | 24/M | acne vulgaris, atopy | no benefit |
| U | 25/M | acne vulgaris | leveled chest cysts |
| V | 19/F | acne vulgaris | cleared treated papules |
| W | 21/M | acne vulgaris | leveled large cysts |
| X | 32/F | chin acne, seborrhea | cleared old cysts |
| Y | 25/F | acne, seborrhea | 70% of cysts reduced in 7 days |

Ordinarily the compositions can contain from about 0.5 to about 2% by weight of nitrate or nitrite, preferrably from about 0.5 to 1%. The remainder of the composition will comprise carriers suitable for ointment or gel formulations well known in this field; see e.g.; U.S. Pat. No. 4,318,907. Since, however, systemic vasodilating activity is not desired in the present invention, formulation which enhance percutaneous bioavailability should be avoided, see e.g., U.S. Pat. No. 4,322,433. Suitable carriers include ointment bases such as lanolin, higher alkyl alcohols, petrolatum and similar lipophilic materials. A typical formulation is as follows:

| | |
|---|---|
| Nitroglycerin | 0.5 g. |
| Lanolin | 25.0 g |
| White petrolatum | 74.5 g |

The above ingredients are thoroughly blended producing a homogeneous ointment which is applied to the loci of acne papules one or more times a day.

The above and other compositions of the present invention should be applied sparingly to loci of acne papules. There is no advantage to applying such compositions to large unaffected areas. The amount applied need be only sufficient to effect local vasodilation at the site of the papule while at the same time being less than an amount which normally produces systemic effects.

What is claimed is:

1. The method of treating acne which comprises applying topically to the locus of an acne papule a composition having a therapeutic component consisting essentially of an nitrate or nitrite having local vasodilating activity, said nitrate or nitrite being admixed with a topically acceptable and compatible pharmaceutical carrier, in a quantity sufficient to effect topical vasodilation without systemic vasodilation.

2. The method of claim 1 wherein the vasodilating agent is nitroglycerin.

3. The method of claim 2 wherein the nitroglycerin is present in the carrier in a concentration of from about 0.5 to about 2% by weight of composition.

4. The method of claim 3 wherein the carrier comprises lanolin and petrolatum in a weight ratio of about 3:1.

5. The method of claim 4 wherein the concentration of the nitroglycerin in the carrier is from about 0.5 to about 1%.

* * * * *